(12) United States Patent
Anderson

(10) Patent No.: US 7,077,651 B2
(45) Date of Patent: Jul. 18, 2006

(54) DENTAL IMPLEMENT FOR TOOTH RESTORATIONS

(76) Inventor: Robert Anderson, 11206 Garfield St., Coopersville, MI (US) 49404

(*) Notice: Subject to any disclaimer, the term of this patent is extended or adjusted under 35 U.S.C. 154(b) by 403 days.

(21) Appl. No.: 10/359,967

(22) Filed: Feb. 6, 2003

(65) Prior Publication Data

US 2003/0148245 A1 Aug. 7, 2003

Related U.S. Application Data

(60) Provisional application No. 60/355,578, filed on Feb. 7, 2002.

(51) Int. Cl.
*A61C 5/12* (2006.01)

(52) U.S. Cl. ............... 433/139; 433/39; 433/155
(58) Field of Classification Search ............... 433/39, 433/40, 139, 155, 148, 149, 136, 138
See application file for complete search history.

(56) References Cited

U.S. PATENT DOCUMENTS

| | | | |
|---|---|---|---|
| 2,651,841 A | 9/1953 | Peterson | 32/63 |
| 2,700,220 A * | 1/1955 | Peterson | 433/39 |
| 5,607,302 A | 3/1997 | Garrison | 433/39 |
| 5,697,783 A | 12/1997 | Wilson et al. | 433/23 |
| 6,022,217 A | 2/2000 | Hugo | 433/166 |
| 6,183,248 B1 | 2/2001 | Chishti et al. | 433/6 |
| 6,211,264 B1 | 4/2001 | Lu et al. | 523/116 |
| 6,280,185 B1 | 8/2001 | Palmer et al. | 433/8 |
| 6,293,796 B1 | 9/2001 | Trom et al. | 433/155 |
| 6,325,625 B1 | 12/2001 | Meyer | 433/139 |
| 6,336,810 B1 | 1/2002 | Bertoletti | 433/39 |
| 2003/0129562 A1 * | 7/2003 | Mungcal | 433/149 |

OTHER PUBLICATIONS

Search Report on PCT Patent Application No. PCT/US03/03723, which corresponds to U.S. Appl. No. 10/359,967.

* cited by examiner

*Primary Examiner*—Cary E. O'Connor
(74) *Attorney, Agent, or Firm*—Van Dyke, Gardner, Linn & Burkhart, LLP (57) ABSTRACT

A dental implement includes a wire member that forms a generally ring-shaped portion and first and second ends, which depend from the ring-shaped portion. The ring-shaped portion lies in a plane, with the first and second ends depending from the generally ring-shaped portion in a direction generally orthogonal to the plane. At least a portion of the first end touches at least a portion of the second end when in an initial resting state, wherein the first and second ends generate an inward force towards each other when separated.

28 Claims, 8 Drawing Sheets

DENTAL IMPLEMENT FOR TOOTH RESTORATIONS

TECHNICAL FIELD AND BACKGROUND OF THE INVENTION

This application incorporates by reference in its entirety pending U.S. provisional Pat. application entitled DENTAL IMPLEMENT FOR TOOTH RESTORATIONS, Ser. No. 60/355,578, filed Feb. 7, 2002.

The present application relates to a dental implement and, more particularly, to a retaining device, which is used to separate teeth and, further, to hold a contour band in place around a tooth when a cavity in the tooth is to be filled.

When a tooth includes a decayed portion, the decayed portion is excavated and then filled. When the decayed portion is located near its interproximal area between an adjacent tooth, the tooth structure is usually insufficient to provide support to the filling material during the filling process. In order to retain the filling material in the cavity while it hardens, a tooth reconstruction element (typically a thin band, which is usually made of stainless steel or the like) is positioned about the tooth and is secured tightly about the tooth such that the element forms an outer shell or matrix. In this manner, the reconstruction element allows the filling material to fill the excavated portion of the tooth and harden into the correct shape. In addition, in order to accommodate the thickness of the reconstruction element and the shrinkage of the filling material (typically a composite resin) as the filling material cures, the adjacent teeth must be separated.

Numerous implements have been developed to separate teeth and to hold bands in place about a tooth. For example, open-ended rings, such as described in U.S. Pat. No. 6,336,810 to Bertoletti and U.S. Pat. No. 6,325,625 to Meyer, are positioned around the tooth and include downwardly extending tines that are urged between the teeth to separate the teeth and, further, to secure the band against the selected tooth. In order to position the ring, the tines are separated, which causes the ring to generate an inward spring force. However, when the tines are moved between their initial, unloaded state to their separated, loaded state, over time, it has been found that these rings undergo significant and appreciable plastic deformation and, consequently, lose their resilience and strength. Therefore, over time, the rings lose their ability to generate a sufficient force to properly hold the band in place against the tooth and, further, to generate sufficient force to separate the teeth.

Consequently, there is a need for a retaining device that will generate a sufficient force to separate the teeth and hold a band in place against a tooth while retaining its resilience over greater period of time so that it can be used repeatedly.

SUMMARY OF THE INVENTION

The present invention relates to a retaining device with a ring-shaped body and a pair of prongs or tines that depend from the ring-shaped body. The prongs or tines are touching in their initial uninstalled state and, preferably, are pre-stressed or pre-loaded, such that the tines generate an inward force even when in their uninstalled configuration. As a result, the retaining device generates a greater separating force when positioned between adjacent teeth and, further, for these and other reasons described below, exhibits and retains greater resilience and strength over the life of the retaining device.

According to one form of the invention, a dental implement comprises a wire member, which forms a generally ring-shaped portion and first and second ends. The first and second ends depend from the ring-shaped portion in a direction that is generally orthogonal to the plane of the ring-shaped portion. At least a portion of the first end touches at least a portion of the second end when in an initial resting or uninstalled state. Furthermore, the first and second ends generate an inward force towards each other when separated. In this manner, when the implement is positioned around one or more teeth and the ends are inserted between two teeth, the first and second ends will generate a separating force to the teeth.

In one aspect, the wire member has a round or oval cross-section. For example, a suitable oval cross-section has a width dimension that extends in the plane of the ring-shaped portion and that is less than the height dimension of the cross-section, which is perpendicular to the width dimension. The width dimension may be in a range of about 0.9 mm to 1.9 mm and, more preferably, approximately 1.45 mm.

In one aspect, the first and second ends are at least approximately equal in length.

In yet other aspects, the first end and the second end are aligned in a plane which is angled in a first offset plane with respect to the plane of the generally ring-shaped portion at an angle in a range of about 84° to 89°. In yet another aspect, each of the first and second ends is angled in the first offset plane with respect to the plane of the generally ring-shaped portion in a range of about 92.50° to 97.5°.

In another form of the invention, a dental implement comprises a ring-shaped portion having first and second ends, a first depending portion extending from the first end of the ring-shaped portion, and a second depending portion extending from the second end of the ring-shaped portion. The first depending portion applies a spring force to the second depending portion in an initial resting state whereby at least a portion of the first depending portion contacts at least a portion of the second depending portion. In this manner, the depending portions and the ring-shaped portion are pre-stressed.

In one aspect, the first depending portion includes a distal end, which touches at least a portion of the second depending portion. In a further aspect, the distal end of the first depending portion touches the distal end of the second depending portion. In other aspects, at least one of the distal ends of the depending portions is enlarged along at least one axis.

According to yet another form of the invention, a dental implement comprises a generally ring-shaped portion and first and second ends. The first and second ends depend from the ring-shaped portion in a direction that is generally orthogonal to the plane of the ring-shaped portion. At least a portion of the first end touches at least a portion of the second end when in an initial resting state. Furthermore, the first and second ends are adapted to generate an inward force in a range of approximately 20 N to 48 N and, more preferably, approximately 20 N to 40 N when separated.

In one aspect, the first and second ends are preferably preloaded so that when the first and second ends are in their initial resting state, the first and second ends generate an inward force towards each other to thereby induce a preload or prestress in the ring shaped portion.

In another aspect, the first and second ends are adapted to generate a force in a range about 28 N to 34 N at a separation distance of about 6 mm when the first and second ends are initially separated to a distance of about 8 mm.

In yet another form of the invention, a dental implement is formed by a wire that is bent into a generally ring shaped configuration to form a generally ring-shaped portion with its ends bent in a direction that is generally orthogonal to the plane of the ring-shaped portion. During the forming, the ends are overlapped by about 10° to 100° and, more preferably, by about 30° to 80° past the point where they would initially contact in their initial formed state, and as a result, when aligned and moved to their initial uninstalled state generate a preload or pre-stress in the ends and, further, in the ring-shaped portion. The ends have a stored energy such that when the ends are separated for placement around one or more teeth, they generate an inward force towards each other in a range of approximately 20 N to 48 N, more preferably, approximately 20 N and 40 N. Preferably, the wire is rolled to reduce the stresses in the wire. In addition, the implement is preferably heat treated at a temperature in a range of about 300° C. to 500° C. for a period in a range of about 30 minutes to 90 minutes. Optionally, the implement is electro-polished and, thereafter, subject to a second heat treatment at a temperature in a range of about 320° C. to 480° C. for a period of about 15 to 45 minutes.

From the foregoing, it can be appreciated that the dental implement of the present invention provides a retaining device that generates a greater separating force than devices heretofore known and, furthermore, exhibits and retains greater resilience and strength over the life of the retaining device.

These and other objects, advantages, purposes, and features of the invention will become more apparent from the study of the following description taken in conjunction with the drawings.

DETAILED DESCRIPTION OF THE DRAWINGS

DETAILED DESCRIPTION OF THE PREFERRED EMBODIMENTS

Figure 1:
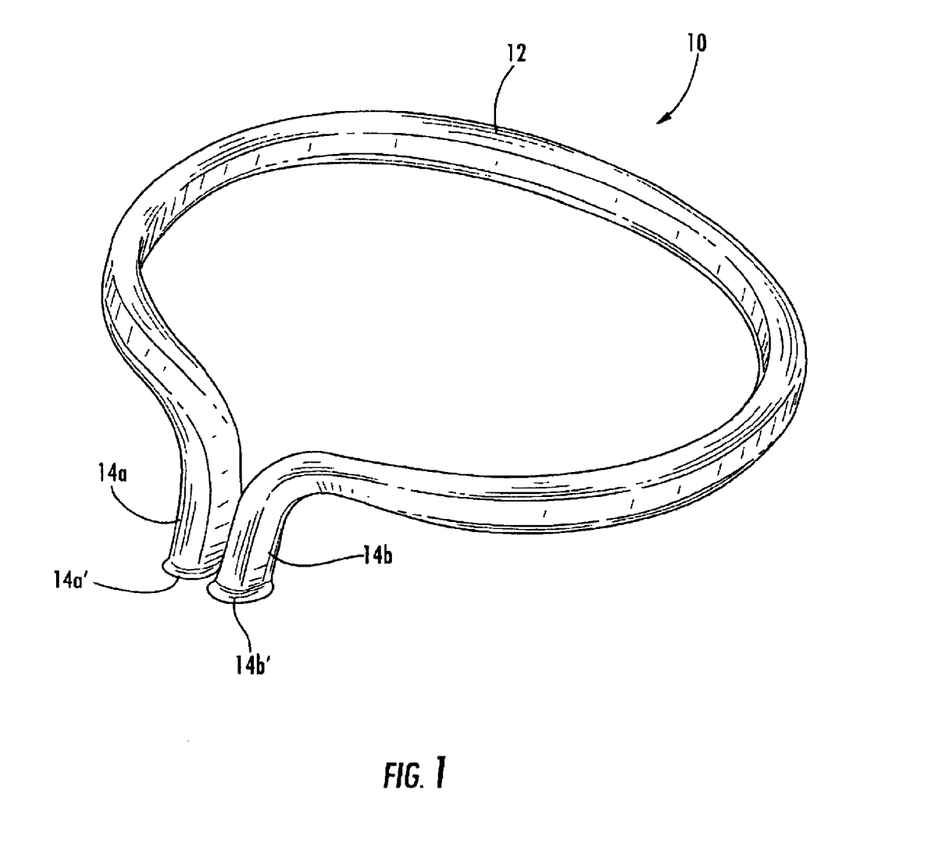
FIG. 1 is a perspective view of the dental implement of the present invention.

Referring to FIG. 1, the numeral 10 generally designates a dental implement of the present invention. Dental implement 10 comprises a retaining device for retaining a band or matrix against a tooth undergoing repair. Dental implement 10 includes generally ring-shaped portion 12 and a pair of downwardly depending prongs or tines 14a and 14b. As will be more fully described below, tines 14a and 14b are formed such that at least a portion of the tines touch when the implement is in its initial uninstalled state. As a result, the amount of force needed to move or separate the tines from their initial uninstalled state to an installed state is greater than conventional open-ended ring-type implements. Further, implement 10 retains its resiliency so that the implement can be reused and reinserted without losing its resiliency and strength needed to separate the teeth.

Figure 2:
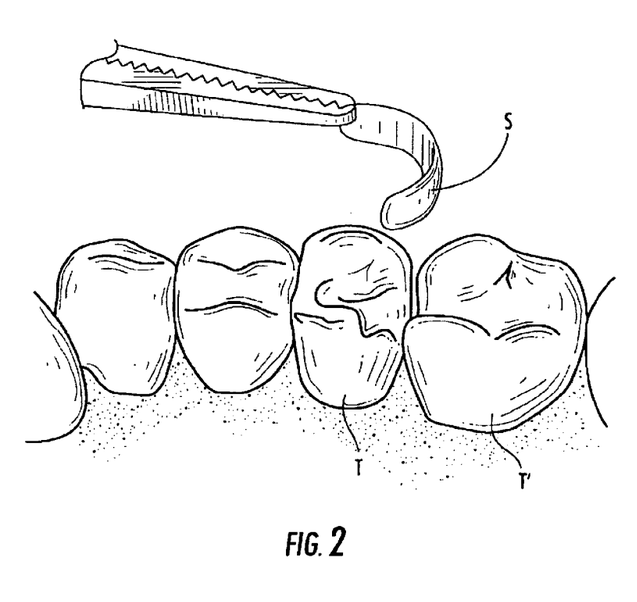
FIG. 2 is a perspective view illustrating a tool reconstruction element, such as a band, being positioned adjacent a tooth that is to undergo restoration.
Figure 3:
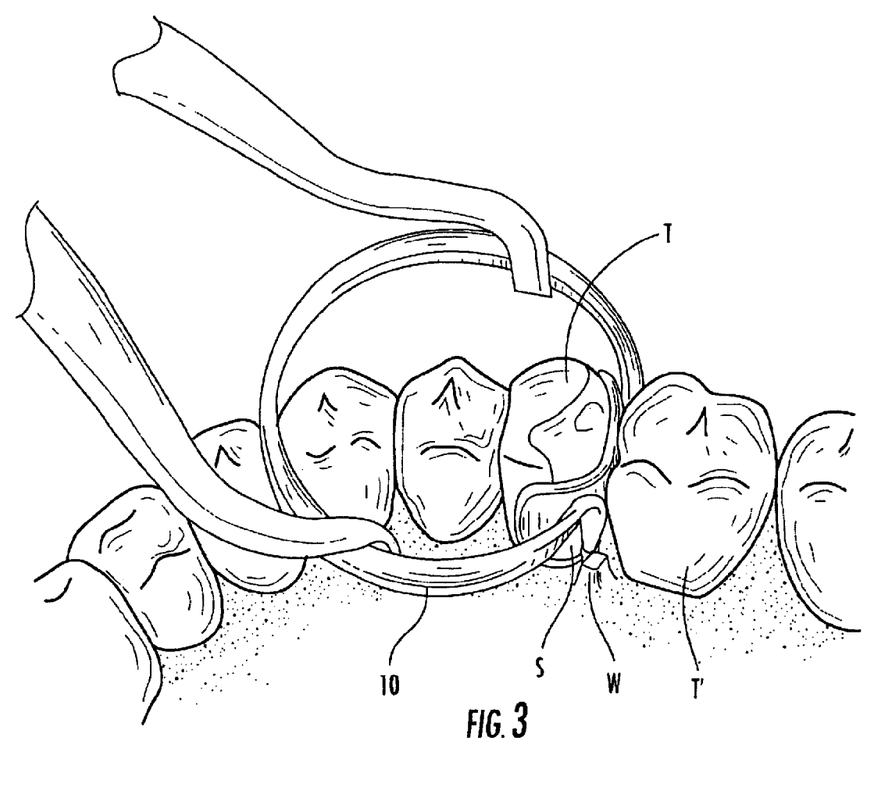
FIG. 3 is a perspective view similar to FIG. 2 illustrating a spreading tool placing the dental implement of FIG. 1 in position between the adjacent teeth.
Figure 4:
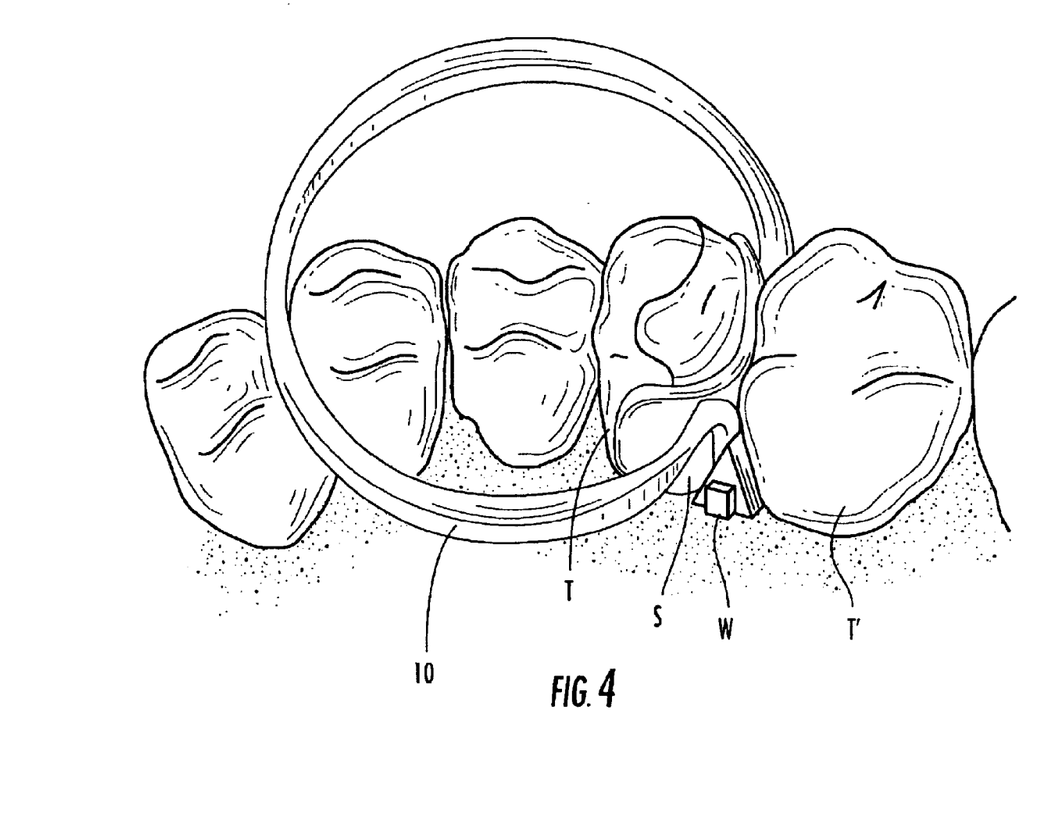
FIG. 4 is a similar view to FIG. 3 illustrating the band in place between the adjacent teeth and the dental implement of FIG. 1 being in position to hold the band against the tooth and, further, to spread the adjacent teeth.

Referring to FIGS. 2-5, when a mesial or distal interproximal area of a tooth T' needs to be repaired or restored, a temporary support S, such as a shield or band, is placed between tooth T' and an adjacent tooth T so that the support will retain the filling in the excavated cavity of the tooth. As best seen in FIG. 2, support S is placed between the adjacent teeth by a dental tool. Once the support (S) is in place, the dental implement 10 of the present invention, which has been separated by another dental tool (FIG. 3), is placed such that its prongs or tines 14a and 14b are positioned between the adjacent teeth. When separated and placed between the teeth, the prongs generate an inward force that urges the two teeth to separate and, further, presses the support against the tooth undergoing restoration. Optionally, a wedge W may be placed between the teeth (T and T') with the prongs positioned between the wedge and the support to further enhance sealing of the support against tooth T.

In preferred form, support S comprises a thin metal band, such as stainless steel or silver band, which typically has a thickness in a range of about 0.025 mm to 0.080 mm. In addition, the band is preferably heat-treated to a temperature in a range of about 600° F. to 950° F., more preferably, about 800° F. The band is heat-treated for a period in a range of about 6 minutes to 30 minutes, more preferably, for about 12 minutes.

Figure 5:
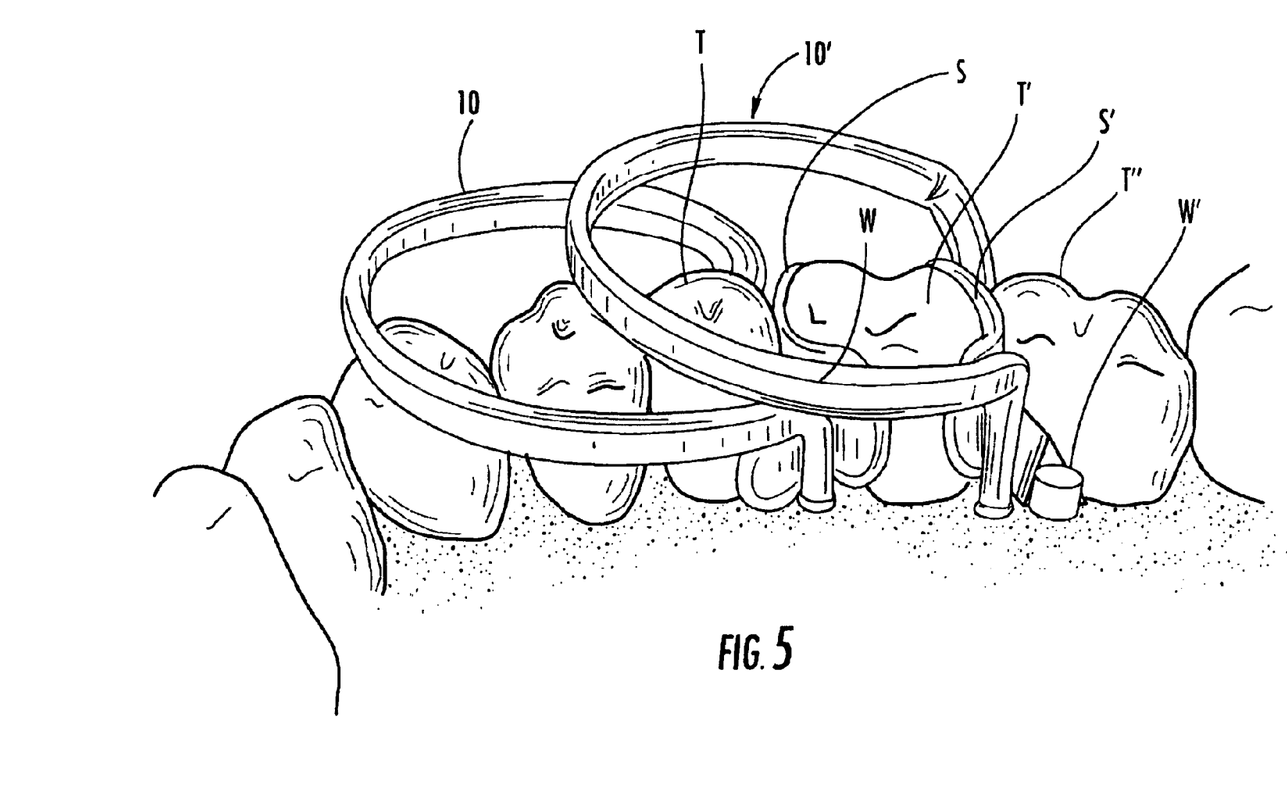
FIG. 5 is a perspective view of the dental implement of FIG. 1 and a second dental implement of the present invention being used concurrently on a tooth that has decay on both interproximal areas of the tooth.
Figure 10:
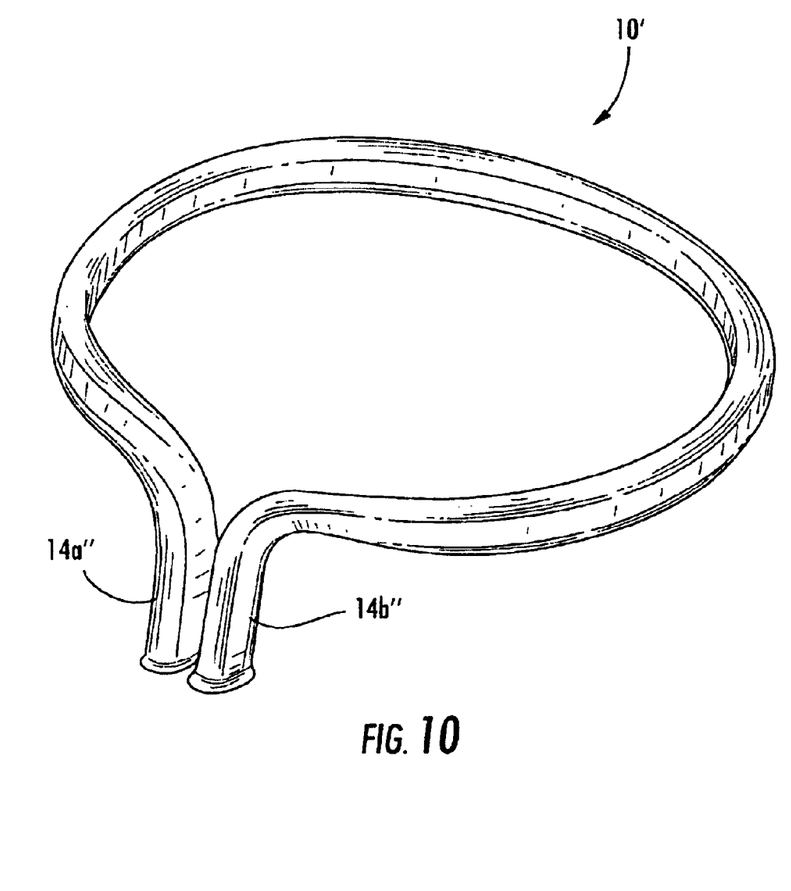
FIG. 10 is a perspective view of the second dental implement of FIG, 5.

Referring to FIG. 5, where a tooth has decay on both sides, a second support S' or band may be positioned adjacent the other side of the tooth with a second dental implement 10' positioned on top of the first implement and on the distal side with its tines adjacent the second support for holding the second support or band against the opposed side of the tooth. Similar to implement 10, implement 10' will urge tooth T' and adjacent tooth T" to separate and hold support S' in place. Optionally, a second wedge W' may be inserted between teeth T' and T" to further seal support S' against tooth T'. In this application, it is generally preferred that implement 10' (FIG. 10), which is of similar construction to implement 10, have longer prongs or tines 14a" and 14b" to ease stacking of the implements. For example as described below, the lengths of tines 14a and 14b of implement 10 are preferably in a range of about 5.0 mm to 8.5 mm and, most preferably, about 7.3 mm. The tines of implement 10' preferably have lengths in a range of approximately 8 mm to 12 mm and, more preferably, about 9.75 mm. In addition, the lengths of the tines of a respective implement are preferably within ±0.75 mm of each other, and more preferably are approximately equal.

Figure 6:
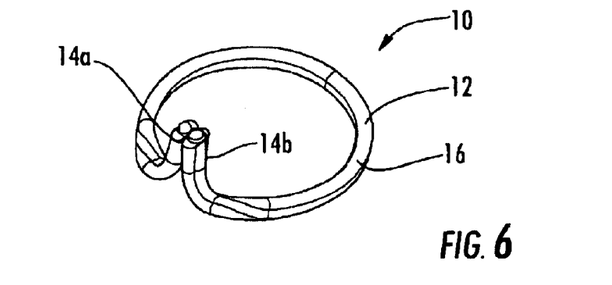
FIG. 6 is a bottom perspective view of the dental implement of FIG. 1.
Figure 8:
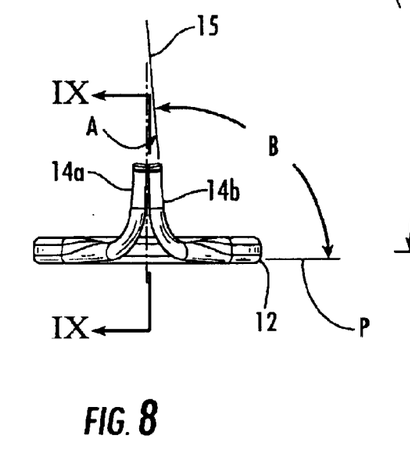
FIG. 8 is an inverted elevation view of the dental implement of FIG. 1.

Referring to FIG. 6, dental implement 10 is formed from an extruded wire 16, such as a stainless steel spring wire. However, it can be appreciated that other materials, including titanium, titanium based material, such as titanium nickel, or a hybrid material, such as a hybrid plastic material, may be used as well. Wire 16 is preferably rolled and formed into an annular shape in which its distal end portions are twisted and then bent downwardly (as viewed in FIG. 1) or upwardly (as viewed in FIG. 6) to form tines 14*a* and 14*b*. In the illustrated embodiment, tines 14*a* and 14*b* are formed by twisting the end portions of the wire inwardly generally toward the center of the ring-shaped portion and then downwardly or upwardly depending on the orientation of the implement. Preferably, the end portion of wire 16 is twisted inwardly in a range of about 80° to 100° before bending to form tines 14*a* and 14*b*. Most preferably, the end portions of wire 16 are twisted approximately 90° before being bent to form tines 14*a* and 14*b*. In addition, as best seen in FIG. 8, tines 14*a* and 14*b* are bent so that they are angled with respect to axis 15 at angle A in a range of about 0° to 10° and, more preferably, about 5° so that tines 14*a* and 14*b* converge along axis 15. In addition, ring-shaped portion 12 lies in a plane P, with tines 14*a* and 14*b* bent at an angle B with respect to plane P in a range of about 90° to 100° and, more preferably, in a range of about 92.5° to 97.5° (with tine 14*a* bent in a clockwise direction from plane P, and tine 14*b* bent in a counter clockwise direction from plane P as viewed in FIG. 8). Furthermore, referring to FIG. 9, tines 14*a* and 14*b* are aligned in an offset plane P' that is angled upwardly from plane P at an angle C in a range of approximately 80° to 90° and, more preferably, in a range of approximately 84° to 89°, and most preferably, about 87°.

In addition, in order to increase the tines' grip on the teeth and support S, the distal end portions of tines 14*a* and 14*b* are optionally burnished or rolled such that distal end portions 14*a*' and 14*b*' form flanges 22 or are enlarged along at least one axis, such as a y-axis 20*a*, 20*b* (FIG. 7), and may extend along both x- and y-axes 20*a*', 20*b*', 20*a*, and 20*b*. Preferably, axes 20*a*' and 20*b*' of tines 14*a* and 14*b* are substantially collinear, as will be more fully described below. The size or overhang of the burnish or flange (beyond the perimeter of the tines) is preferably in a range of 0.05 mm to 0.25 mm and, more preferably, about 0.1 mm. It should be understood that the enlarged portion may project outwardly around the full circumference of the tine or just over one or more discrete portions of the respective tine's perimeter and, further, may extend in the z-axis (20*a*" and 20*b*") as well. Alternately, distal ends 14*a*' and 14*b*' may include slightly bulbous ends that are coated or otherwise sheathed in a high friction substance, such as disclosed in U.S. Pat. No. 5,607,302, which is herein incorporated by reference in its entirety.

Figure 7:
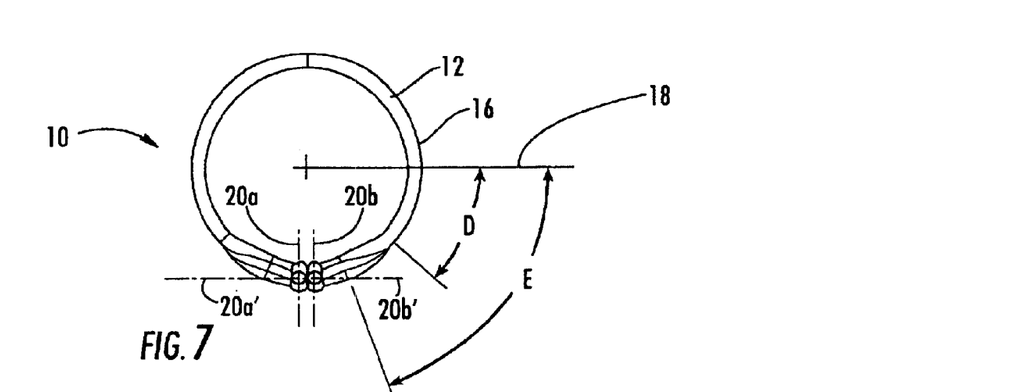
FIG. 7 is a bottom plan view of the dental implement of FIG. 1.

Referring to FIG. 7, wire 16 is twisted starting at an angle D in a range of about 25° to 60° and, most preferably, at approximately 41° from transverse central axis 18. Furthermore, the twist in wire 16 terminates at approximately at an angle E in a range of about 60° to 85° and, most preferably, at an angle of approximately 70° from axis 18. The height of tines 14*a* and 14*b* may be varied as needed, but typically range from about 5.0 mm to 8.5 mm and, for example, more typically are approximately 7.3 mm, with the lengths of the tines preferably within ±0.75 mm of each other, and more preferably approximately equal.

Figure 9:
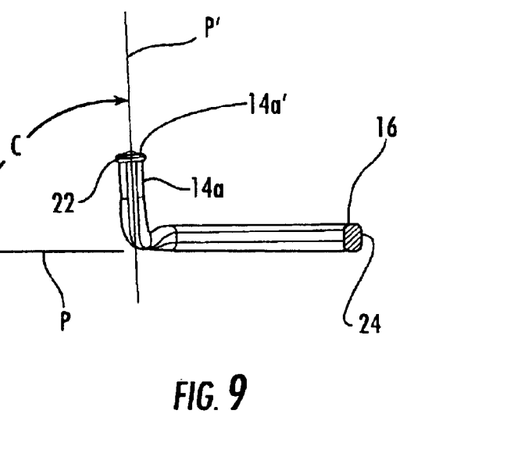
FIG. 9 is a side elevation view of the dental implement illustrated in FIG. 8.

As best seen in FIG. 9, in the illustrated embodiment, wire 16 has a rounded cross-section and, preferably, a generally oval cross-section 24 with a width dimension in range of approximately 0.9 mm to 1.9 mm and a height dimension in range of approximately 1.6 mm to 3.6 mm. More preferably, wire 16 has a height of approximately 2.3 mm and a width of approximately 1.45 mm. In addition, the inner diameter of ring-shaped portion 12 is in a range of 10 to 30 mm, more preferably, in a range of about 15 to 25 mm, and, most preferably, in range of about 20 to 22 mm. However, it can be appreciated wire 16 can have a round cross-section (such as shown in reference to implement 110 in FIG. 11) or a non-rounded cross-section, such as a flat or rectilinear cross-section. Together, the dimensional properties of the wire and the configuration of the wire result in a dental implement that can generate an increased separating force while not undergoing any significant plastic deformation and, thereby, retaining its resilience and strength over time.

As noted above, wire 16 is preferably rolled wire that is bent into its annular shape with its free ends twisted inwardly followed by its distal ends twisted inwardly and downwardly to form tines 14*a* and 14*b* so that at least a portion of the tines are touching (FIG. 6). Furthermore, the distal ends of wire 16 are bent and twisted such that they overlap so that when aligned (FIG. 6), tines 14*a* and 14*b* generate an inward force in their initial uninstalled state and, therefore, are preloaded or pre-stressed and also preload or pre-stress ring-shaped portion 12. For example, in preferred form, tines 14*a* and 14*b* initially overlap with an angle in a range of about 10° to 100° and, more preferably of about 30° to 80° past the point where they would initially contact. In this manner, implement 10 has stored kinetic or potential energy when in its initial uninstalled state. By preloading or pre-stressing the implement, the dentist or dental technician must exert a greater force to move the prongs or tines from their initial uninstalled state to their spaced apart state for placement between the teeth. This results in an increased separation force exerted on the teeth by tines 14*a* and 14*b*. Furthermore, given the dimensions of the ring-shaped portion and the material (preferably high strength stainless spring steel), wire 16 does not undergo any appreciable or significant plastic deformation and, therefore, does not undergo a significant permanent set when tines 14*a* and 14*b* are separated for placement between the adjacent teeth. In other words, the material forming wire 16 is not stretched to any significant degree when it is opened for placement. As a result, the resilience of the ring is maintained and, further, produces a greater inward force between the tines when the tines are separated. In addition, because of the manufacturing process and the geometry of the implement, tines 14*a* and 14*b* of ring implement 10 may undergo similar displacements to those of the prior art rings without sacrificing the resiliency of implement 10 and, further, can generate a high separation force on the order of approximately 20 N to 60 N, more preferably approximately 20 N to 48 N, most preferably approximately 20 N to 40 N, depending on the separation of the times. For example, testing of the effect of the preload on the tines when the ring is opened to about 8 mm (with the measurement taken at 6 mm) yielded measurements in a range of about 28 N to 34 N. Testing of the effect of the preload on the tines when the ring is opened to about 11 mm (with the measurement taken about 9 mm) yielded measurements on the order of about 25 N to 55 N and, more preferably, in a range of about 30 N to 45 N.

In order to reduce the internal stresses in wire 16, wire 16 is preferably rolled and, as noted above, preferably rolled from a high strength stainless spring steel material. After bending wire 16 into its ring-shape, dental implement 10 is heat-treated at a temperature in a range of about 300° to 500° C. and, more preferably, in a range of about 425° to 450° C. Preferably, dental implement 10 is heat treated for a period of about 30 to 90 minutes and, more preferably, for a period of about one hour. After the initial heat-treatment, wire 16 is electro-polished and then stress relieved by heating to a temperature of about 320° to 480° C., more preferably, by heating to a temperature of about 340° to 400° and, most preferably at about 360° C. for about 15 to 45 minutes, more preferably, for about 30 minutes. Furthermore, as noted above when forming tines 14a and 14b, each tine 14a, 14b preferably overlaps in a range of about 10° to 100° and, more preferably, in a range of about 30° to 80°. As a result, when they are aligned, with axes 20a' and 20b' being substantially collinear, the force exerted by tines on each other will be in a range of about 2 to 12 N, more preferably, in a range of about 5 to 10 N. In this manner, as noted above, dental implement 10 is pre-stressed in its initial un-installed state.

Figure 11:
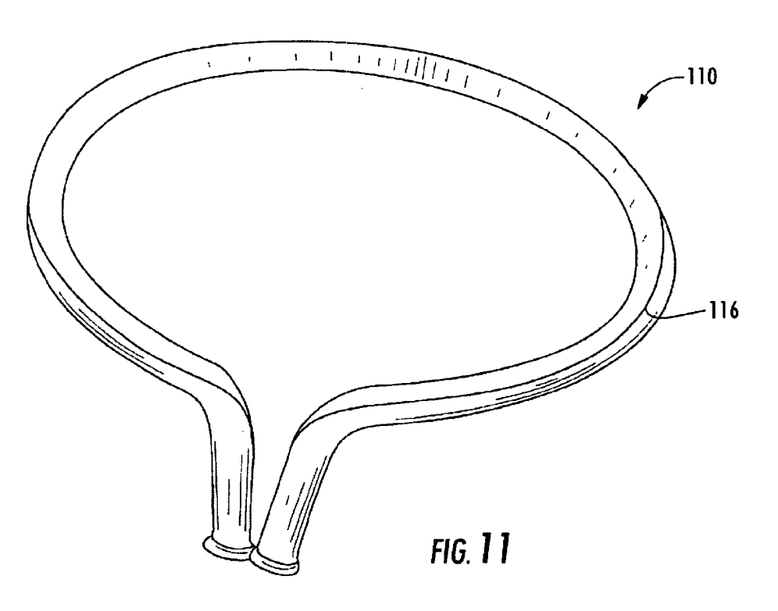
FIG. 11 is perspective view of another embodiment of the dental implement of the present invention.

As noted above, the dental implement of the present invention may have a round cross-section such as illustrated in FIG. 11. Implement 110 is of similar construction to implements 10' and 10 but includes a wire 116 with a round cross-section.

While several forms of the invention have been shown and described, other variations will be appreciated by those of ordinary skill in the art. Therefore, it will-be understood that the embodiments shown in the drawings and described above are merely for illustrative purposes, and are not intended to limit the scope of the invention, which is defined by the claims, which follow as interpreted under the principles of patent law including the doctrine of equivalents.

I claim:

1. A dental implement comprising:
   a ring-shaped portion and first and second ends;
   a first depending portion extending from said first end of said ring-shaped portion;
   a second depending portion extending from said second end of said ring- shaped portion; and
   wherein said first depending portion applies a force to said second depending portion and said second depending portion applies a force to said first depending portion in an initial uninstalled configuration wherein said ring-shaped portion is preloaded with an initial force such that when said depending portions are separated for placement between teeth the ring-shaped portion will generate a separating force greater than said initial force to thereby separate the teeth.

2. The dental implement according to claim 1, wherein said first depending portion is approximately equal in length to said second depending portion.

3. The dental implement according to claim 1, wherein said first depending portion includes a distal end, said second depending portion including a distal end, said distal end of said first depending portion touching at least a portion of said second depending portion.

4. The dental implement according to claim 3, wherein said distal end of said first depending portion touches said distal end of said second depending portion.

5. The dental implement according to claim 4, wherein said ring-shaped portion has a generally round cross-section.

6. The dental implement according to claim 4, wherein said ring-shaped portion has an oval cross-section.

7. The dental implement according to claim 6, wherein said oval cross-section has a width dimension and a height dimension, said width dimension extending along said plane and being less that said height dimension.

8. The dental implement according to claim 7, wherein said width dimension is in a range of about 0.9 to 1.9 mm.

9. The dental implement according to claim 8, wherein said width comprises approximately 1. 45 mm.

10. The dental implement according to claim 3, wherein said distal end of said first depending portion is enlarged along at least one axis.

11. The dental implement according to claim 10, wherein said distal end of said second depending portion is enlarged along at least one axis.

12. The dental implement according to claim 1, wherein said first depending portion and said second depending portion are aligned in a first offset plane angled with respect to said plane of said generally ring-shaped portion at an angle in a range of about 84 C. to 89 C., wherein said dental implement may be used in conjunction and stacked with another dental implement.

13. The dental implement according to claim 12, wherein said first depending portion is angled in a second offset plane with respect to said plane of said generally ringed-shaped portion of about 92.5 C. to 97.5 C.

14. The dental implement according to claim 1, wherein said generally ring- shaped portion has a generally oval cross-section.

15. The dental implement according to claim 14, wherein said generally ring- shaped portion lies in a plane, said oval cross-section having a width dimension and a height dimension.

16. The dental implement according to claim 15, wherein said first and second depending portion are at least approximately equal in length.

17. The dental implement according to claim 1, wherein the force between said first and second depending portions in said initial uninstalled configuration is in a range of about 2 N to 12 N.

18. The dental implement according to claim 1, wherein said first depending portion is twisted inwardly generally toward a center of said ring-shaped portion.

19. The dental implement according to claim 18, wherein said second depending portion is twisted inwardly generally toward a center of said ring-shaped portion.

20. The dental implement according to claim 1, wherein said first and second depending portions overlap with an angle in a range of 10 C. to 100 C. past the point where they would initially contact when in said uninstalled configuration wherein said ring- shaped portion has stored kinetic energy when in said uninstalled configuration.

21. A dental implement comprising:
   a ring-shaped metal portion having first and second ends;
   a first depending portion extending from said first end of said ring-shaped portion;
   a second depending portion extending from said second end of said ring- shaped portion; and
   wherein said first depending portion and said second depending portion overlap in a range of about 10 degrees to 100 degrees when in a first configuration and contact each other when moved to a second configuration, wherein said first depending portion applies a force to said second depending portion when in said second configuration and said second depending portion applies a force to said first depending portion when in said second configuration wherein said ring-shaped metal portion is preloaded with an initial force when said first and second depending portions are in said second configuration such that when said depending portions are separated for placement between teeth the ring-shaped portion will generate a separating force greater than said initial force to thereby separate the teeth.

22. The dental implement according to claim 21, wherein said first depending portion and said second depending portion overlap in a range of about 30 degrees to 80 degrees when in said first configuration.

23. The dental implement according to claim 21, wherein said first depending portion includes a distal end, said second depending portion including a distal end, said distal end of said first depending portion touching at least a portion of said second depending portion.

24. The dental implement according to claim 21, wherein said distal end of said first depending portion touches said distal end of said second depending portion.

25. The dental implement according to claim 21, wherein said first depending portion and said second depending portion generat a force in a range of 20 N to 48 N when separated.

26. The dental implement according to claim 25, wherein said first depending portion and said second depending portion generate a force in a range of 20 N to 40 N when separated.

27. The dental implement according to claim 25, wherein said generally ring- shaped portion has a generally overall cross-section.

28. The dental implement according to claim 27, wherein said generally ring-shaped portion lies in a plane, said oval cross-section having a width dimension and a height dimension, said width dimension extending along said plane and being less than said height dimension.

* * * * *

UNITED STATES PATENT AND TRADEMARK OFFICE
CERTIFICATE OF CORRECTION

PATENT NO. : 7,077,651 B2  Page 1 of 1
APPLICATION NO. : 10/359967
DATED : July 18, 2006
INVENTOR(S) : Robert Anderson It is certified that error appears in the above-identified patent and that said Letters Patent is hereby corrected as shown below:

Column 2:
Line 28, "92.50°" should be --92.5°--.

Column 7:
Line 17, "will-be" should be --will be--.
Line 25, Claim 1, Delete --and-- in the first occurrence.
Line 25, Claim 1, Insert --having-- after "portion".
Line 61, Claim 9, Insert --dimension-- after "width".
Line 61, Claim 9, "1. 45" should be --1.45--.

Column 8:
Line 5, Claim 12, "84 C to 89 C" should be --84° to 89°--.
Line 10, Claim 13, "ringed-shaped" should be --ring-shaped--.
Line 11, Claim 13, Insert --in a range-- after "portion".
Line 11, Claim 13, "92.5 C to 97.5 C" should be --92.5° to 97.5°--.
Line 13, Claim 14, "ring- shaped" should be --ring-shaped--.
Line 16, Claim 15, "ring- shaped" should be --ring-shaped--.
Line 17, Claim 15, Insert --, said width dimension extending along said plane and being less than said height dimension.-- after "dimension" in the second occurrence.
Line 20, Claim 16, "portion" should be --portions--.
Line 34, Claim 20, "10 C. to 100 C." should be --10° to 100°--.
Line 35, Claim 20, "ring- shaped" should be --ring-shaped--.

Column 9:
Line 6, Claim 25, "generat" should be --generate--.

Column 10:
Line 2, Claim 27, "10 C. to 100 C." should be --10° to 100°--.
Line 2, Claim 27, "overall" should be --oval--.

Signed and Sealed this

Thirtieth Day of January, 2007

JON W. DUDAS
*Director of the United States Patent and Trademark Office*